(12) United States Patent
Yong et al.

(10) Patent No.: US 9,213,029 B2
(45) Date of Patent: Dec. 15, 2015

(54) METHOD FOR DIAGNOSING BREAST CANCER BY DETECTION OF POLYMERIC IMMUNOGLOBULIN RECEPTOR IN VESICLES ISOLATED FROM PATIENTS

(71) Applicant: Samsung Electronics Co., Ltd., Suwon-si, Gyeonggi-do (KR)

(72) Inventors: Ye-ryoung Yong, Seoul (KR); Ga-hee Kim, Yongin-si (KR); Hyun-ju Kang, Hwaseong-si (KR)

(73) Assignee: SAMSUNG ELECTRONICS CO., LTD., Suwon-Si (KR)

(*) Notice: Subject to any disclaimer, the term of this patent is extended or adjusted under 35 U.S.C. 154(b) by 0 days.

(21) Appl. No.: 14/215,743

(22) Filed: Mar. 17, 2014

(65) Prior Publication Data

US 2014/0377779 A1 Dec. 25, 2014

(30) Foreign Application Priority Data

Jun. 25, 2013 (KR) .................. 10-2013-0073320
Nov. 5, 2013 (KR) .................. 10-2013-0133822

(51) Int. Cl.
*G01N 33/574* (2006.01)
*C07K 16/30* (2006.01)
*C07K 16/28* (2006.01)
*C12N 5/07* (2010.01)

(52) U.S. Cl.
CPC ........ *G01N 33/57415* (2013.01); *C07K 16/283* (2013.01); *G01N 2333/70535* (2013.01)

(58) Field of Classification Search
None
See application file for complete search history.

(56) References Cited

U.S. PATENT DOCUMENTS

| | | | |
|---|---|---|---|
| 7,255,874 B1 * | 8/2007 | Bobo et al. | 424/450 |
| 7,897,356 B2 | 3/2011 | Klass et al. | |
| 8,216,784 B2 | 7/2012 | Taylor et al. | |
| 2007/0243540 A1 * | 10/2007 | Tsai et al. | 435/6 |
| 2012/0058492 A1 | 3/2012 | Lozupone et al. | |
| 2012/0295286 A1 * | 11/2012 | Berg | 435/7.92 |
| 2013/0045220 A1 | 2/2013 | Jiang | |
| 2014/0148350 A1 | 5/2014 | Spetzler et al. | |

FOREIGN PATENT DOCUMENTS

| | | | | |
|---|---|---|---|---|
| KR | 1020130022204 A | 3/2013 | | |
| WO | WO2010127399 | * 11/2010 | ............ | C12Q 1/68 |
| WO | WO2011150994 | * 12/2011 | .......... | G01N 33/574 |
| WO | WO 2012/024543 A1 | 2/2012 | | |
| WO | WO 2012/031008 A1 | 3/2012 | | |
| WO | WO2012174970 | * 12/2012 | .......... | G01N 33/574 |

OTHER PUBLICATIONS

Herrnring et al., Expression of the apoptosis-inducing ligands FasL and TRAIL in malignant and benign human breast tumors, Histochem Cell Biol., 113, 189-194, 2000.*
Crew et al., Genetic polymorphisms in the apoptosis-associated genes FAS and FASL and breast cancer risk, 28, 2548-2551, 2007.*
English translation of WO2012174970, Mar. 31, 2015.*
Piskurich et al., Molecular Cloning of the Mouse Polymeric Ig Receptor, *The Journal of Immunology*, 154:1735-1747 (1995).
Verbeet et al., Cloning and characterization of the bovine polymeric immunoglobulin receptor-encoding cDNA, *Gene*, 164: 329-333 (1995).
Springer-Verlag, Tumor and Staging Data, *AJCC Cancer Staging Manual*, Sixth Ed., pp. 123-168F (2002).

* cited by examiner

*Primary Examiner* — Elly-Gerald Stoica
(74) *Attorney, Agent, or Firm* — Leydig, Voit & Mayer, Ltd.

(57) ABSTRACT

A composition for breast cancer diagnosis using a material specifically binding to a polymeric immunoglobulin receptor (PIGR) or a fragment thereof, and a method for detecting breast cancer or acquiring information for breast cancer diagnosis using the composition.

10 Claims, 5 Drawing Sheets

SEQUENCE LISTING

```
<160> NUMBER OF SEQ ID NOS: 1

<210> SEQ ID NO 1
<211> LENGTH: 764
<212> TYPE: PRT
<213> ORGANISM: Homo sapiens

<400> SEQUENCE: 1

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60
```

-continued

```
Ile Thr Leu Ile Ser Ser Glu Gly Tyr Val Ser Lys Tyr Ala Gly
 65                  70                  75                  80

Arg Ala Asn Leu Thr Asn Phe Pro Glu Asn Gly Thr Phe Val Val Asn
             85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
            115                 120                 125

Gln Gly Pro Gly Leu Leu Asn Asp Thr Lys Val Tyr Thr Val Asp Leu
130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
            195                 200                 205

Gln Leu Arg Leu Ser Asp Ala Gly Gln Tyr Leu Cys Gln Ala Gly Asp
210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
            275                 280                 285

Arg Ala Pro Ala Phe Glu Gly Arg Ile Leu Leu Asn Pro Gln Asp Lys
290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Gly Ser Val Ala
            355                 360                 365

Val Leu Cys Pro Tyr Asn Arg Lys Glu Ser Lys Ser Ile Lys Tyr Trp
370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
            435                 440                 445

Trp Arg Thr Thr Val Glu Ile Lys Ile Ile Glu Gly Glu Pro Asn Leu
450                 455                 460

Lys Val Pro Gly Asn Val Thr Ala Val Leu Gly Glu Thr Leu Lys Val
465                 470                 475                 480
```

-continued

```
Pro Cys His Phe Pro Cys Lys Phe Ser Ser Tyr Glu Lys Tyr Trp Cys
            485             490             495

Lys Trp Asn Asn Thr Gly Cys Gln Ala Leu Pro Ser Gln Asp Glu Gly
        500             505             510

Pro Ser Lys Ala Phe Val Asn Cys Asp Glu Asn Ser Arg Leu Val Ser
        515             520             525

Leu Thr Leu Asn Leu Val Thr Arg Ala Asp Glu Gly Trp Tyr Trp Cys
    530             535             540

Gly Val Lys Gln Gly His Phe Tyr Gly Glu Thr Ala Ala Val Tyr Val
545             550             555                         560

Ala Val Glu Glu Arg Lys Ala Ala Gly Ser Arg Asp Val Ser Leu Ala
            565             570             575

Lys Ala Asp Ala Ala Pro Asp Glu Lys Val Leu Asp Ser Gly Phe Arg
            580             585             590

Glu Ile Glu Asn Lys Ala Ile Gln Asp Pro Arg Leu Phe Ala Glu Glu
            595             600             605

Lys Ala Val Ala Asp Thr Arg Asp Gln Ala Asp Gly Ser Arg Ala Ser
    610             615             620

Val Asp Ser Gly Ser Ser Glu Glu Gln Gly Gly Ser Ser Arg Ala Leu
625             630             635                         640

Val Ser Thr Leu Val Pro Leu Gly Leu Val Leu Ala Val Gly Ala Val
            645             650             655

Ala Val Gly Val Ala Arg Ala Arg His Arg Lys Asn Val Asp Arg Val
            660             665             670

Ser Ile Arg Ser Tyr Arg Thr Asp Ile Ser Met Ser Asp Phe Glu Asn
    675             680             685

Ser Arg Glu Phe Gly Ala Asn Asp Asn Met Gly Ala Ser Ser Ile Thr
    690             695             700

Gln Glu Thr Ser Leu Gly Gly Lys Glu Glu Phe Val Ala Thr Thr Glu
705             710             715                         720

Ser Thr Thr Glu Thr Lys Glu Pro Lys Lys Ala Lys Arg Ser Ser Lys
            725             730             735

Glu Glu Ala Glu Met Ala Tyr Lys Asp Phe Leu Leu Gln Ser Ser Thr
            740             745             750

Val Ala Ala Glu Ala Gln Asp Gly Pro Gln Glu Ala
            755             760
```

METHOD FOR DIAGNOSING BREAST CANCER BY DETECTION OF POLYMERIC IMMUNOGLOBULIN RECEPTOR IN VESICLES ISOLATED FROM PATIENTS

CROSS-REFERENCE TO RELATED APPLICATIONS

This application claims the benefit of Korean Patent Application No. 10-2013-0073320, filed on Jun. 25, 2013, and Korean Patent Application No. 10-2013-0133822, filed on Nov. 5, 2013, in the Korean Intellectual Property Office, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 7,060 Bytes ASCII (Text) file named "715791_ST25.TXT," created on Mar. 11, 2014.

BACKGROUND

1. Field

The present invention relates to compositions for breast cancer diagnosis comprising a material that specifically binds to a polymeric immunoglobulin receptor (PIGR) protein or a fragment thereof, and a method of diagnosing a breast cancer using said compositions.

2. Description of the Related Art

Microvesicles are small membranous vesicles that exist in or are secreted from various types of cells. Microvesicles secreted from cells include: (i) exosomes, which are vesicles having a diameter from about 30 to about 100 nm; (ii) ectosomes (also called shedding microvesicles (SMVs)), which are vesicles that are released directly from the plasma membranes and have a diameter from about 50 to about 1000 nm; and (iii) apoptotic blebs, which are vesicles secreted from dying cells that have a diameter from about 50 to about 5000 nm.

It has been confirmed through electron microscopy that exosomes are not directly released from a plasma membrane, but rather originate from specific intracellular regions called multivesicular bodies (MVBs), and are then released into the extracellular environment as exosomes. Although it has not yet been clearly determined which molecular mechanisms and pathways are involved in the generation of exosomes, it is known that red blood cells, other various kinds of immune cells, including B-lymphocytes, T-lymphocytes, dendritic cells, blood platelets, and macrophages, and even tumor cells, are able to produce and secret exosomes when in vivo. Exosomes are also known to be separated and excreted from different cell types depending on whether they are in normal states, pathologic states, or abnormal states.

Exosomes comprise surface proteins, which may be used for detection and analysis of the status (e.g., health) of individual cells or organisms. The status of cells or organisms may comprise a disease state, for example, cancer, hereditary diseases, heart diseases, or neuronal diseases (e.g., schizophrenia).

Existing breast cancer diagnosis methods are invasive and thus, are painful to patients. Additionally, existing breast cancer diagnosis methods are very costly, which may prohibit individuals that cannot afford such methods to have less frequent checkups. High accuracy blood tests that utilize blood protein markers for early stage breast cancer diagnosis are not currently available. Circulating tumor cells (CTCs), which comprise blood protein markers useful for the diagnosis of breast cancer, are produced in the metastatic stages of breast cancer, which is often too late to be of use to an individual.

Therefore, a need remains for less invasive compositions and methods for the early diagnosis and selective screening of breast cancer utilizing specific blood markers.

SUMMARY

Provided is a composition or a kit for diagnosing breast cancer, wherein the composition or kit comprises a material that specifically binds to a polymeric immunoglobulin receptor (PIGR) or a fragment thereof.

Also provided is a method for detecting breast cancer in a subject, the method comprising contacting a sample from a subject with a material that specifically binds to a PIGR or a fragment thereof, whereby the material binds to vesicles in the sample that comprise PIGR; measuring the amount material bound to PIGR or a fragment thereof in the sample to determine the amount of PIGR or a fragment thereof present in the sample; and comparing the amount of PIGR or fragments thereof in the sample to a control. Related methods and compositions also are provided.

Additional aspects of the present invention will be set forth in part in the description which follows and, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION OF THE INVENTION

Figure 1:
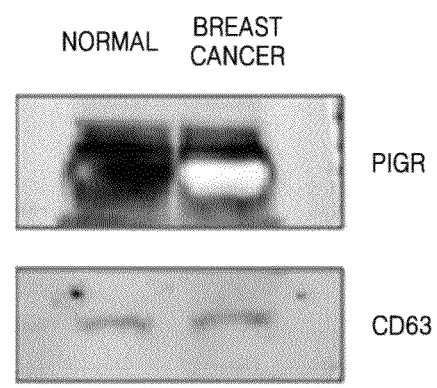
FIG. 1 is a picture of a Western blot illustrating vesicles obtained from a normal person and a breast cancer patient that have been western blotted using an anti-PIGR antibody and an anti-CD63 antibody.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Provided is a composition for breast cancer diagnosis, the composition comprising a material that specifically binds to a polymeric immunoglobulin receptor (PIGR) protein or a fragment thereof.

As used herein, "PIGR" or "PIGR protein" refers to an Fc receptor which facilitates the secretion of immunoglobulin A (IgA) and immunoglobulin M (IgM). The PIGR may mediate intercellular transport of polymeric immunoglobulin molecules. The PIGR comprises 5 units with homology to the variable units of immunoglobulins and comprises a transmembrane region. The PIGR may be linked to a J-chain (joining chain) of dimeric Immunoglobulin A (dIgA). The PIGR is a protein encoded by a PIGR gene. As used herein, "PIGR" or "PIGR protein" refers to a "PIGR" or "PIGR protein" derived from a human or its homologue derived from an animal other than a human. "PIGR" or "PIGR protein" may be mouse, rat, human, bovine, or rabbit PIGR. "PIGR" or "PIGR protein" may have an amino acid sequence of NP_002635 for human and NP_035212 for mouse. "PIGR" or "PIGR protein" may be encoded by a nucleotide sequence of NM_002644 for human and NM_011082 for mouse. "PIGR" or "PIGR protein" may have a conserved functional regions of the molecule, for example, in the extracellular region, conserved motifs include: a 23-amino acid PIG-binding site, 11 intradomain disulfide bonds, consensus sites for N-glycosylation, and a putative cleavage site at which the extracellular region of PIGR (secretory components) is released from the plasma membrane. A 10-amino acid sequence within the transmembrane region is highly conserved, possibly reflecting a mechanism for transmitting signals from the extracellular region to the cytoplasmic tail. Conservation within the cytoplasmic tail of PIGR is clustered in motifs that mediate polarized sorting, endocytosis, and transcytosis (Janet F. Piskurich et al, The Journal of Immunology, 1995, 154:1735-1747).

The PIGR or a fragment thereof may be contained in or on a vesicle. As used herein, the term "vesicle" refers to a membranous structure that is surrounded by a lipid bilayer. For example, the term "vesicle" may refer to a microvesicle or an exosome. As used herein the term "microvesicle" refers to a small vesicle with a membranous structure that originates from a cell. The term "microvesicle" may be interchangeably used herein with the term "circulating microvesicle" or "microparticle". Microvesicles may exist in cells or may be secreted from cells. Microvesicles secreted from cells may include exosomes, ectosomes (shedding microvesicles (SMVs)), or apoptotic blebs. Exosomes are membranous vesicles from about 30 nm to about 100 nm diameter that originate from phagocytes. In vivo microvesicles may contain proteins, microRNAs (miRNAs), or messenger RNAs (mRNAs). The PIGR may be a surface protein or a transmembrane protein of a vesicle. The PIGR may specifically exist on a surface of a vesicle derived from a breast cancer patient. The breast cancer patient may be a patient having ER positive breast cancer. The ER positive breast cancer may be luminal A or luminal B. The ER positive breast cancer may be stage I or II. The stage may be determined by a breast cancer staging using the TMN system, which is based on the size of the tumor (T), whether or not the tumor has spread to the lymph nodes (N) in the armpits, and whether the tumor has metastasized (M) (i.e., spread to a more distant part of the body). Larger size, nodal spread, and metastasis have a larger stage number and a worse prognosis. The main stage may be: stage 0, which is a pre-cancerous or marker condition, either ductal carcinoma in situ (DCIS) or lobular carcinoma in situ (LCIS), stages 1-3, which are within the breast or regional lymph nodes, stage 4, which is 'metastatic' cancer that has a less favorable prognosis.

The PIGR or a fragment thereof may be a human PIGR, mouse PIGR, or a fragment thereof. The human PIGR may be a protein having an amino acid sequence of GenBank Accession No. NP_002635. The mouse PIGR may be a protein having an amino acid sequence of GenBank Accession No. NP_0035212. The PIGR may be a protein having an amino acid sequence of SEQ ID NO:1.

The term "fragment of the PIGR" as used herein refers to a polypeptide having a consecutive amino acid sequence of the PIGR. The fragment of the PIGR may have antigenicity, that is, have an epitope. The fragment of the PIGR may be more than 10, 30, 50, 70, 100, 200, 300, 400, 500, 600, or 700 consecutive amino acids of the PIGR in length. The fragment of the PIGR may be a fragment having 10-800, 30-800, 50-800, 70-800, 100-800, 200-800, 300-800, 400-800, 500-800, 600-800, 700-800, 10-600, 30-600, 50-600, 70-600, 100-600, 200-600, 300-600, 400-600, 500-600, 10-400, 30-400, 50-400, 70-400, 100-400, 200-400, 300-400, 10-300, 30-300, 50-300, 70-300, 100-300, or 200-300 amino acids.

The material that specifically binds to the PIGR or a fragment thereof may be an antibody or a fragment thereof (i.e., an antibody fragment), a ligand, a substrate for an enzyme, an inhibitor, an agonist, an antagonist, a cofactor, or any combination thereof. The material may be, for example, an anti-PIGR antibody or an antigen-binding fragment thereof, a J-chain (joining chain) of an antibody, or any combination thereof. The antibody may be a monoclonal antibody or a polyclonal antibody. The antigen-binding fragment may include an antigen-binding region which may be a single-domain antibody, Fab, Fab', or scFv.

The material that specifically binds to the PIGR or a fragment thereof may comprise a detectable tag. The detectable tag may be an optical tag, an electrical tag, a radioactive tag, an enzyme tag, or any combination thereof. The optical tag may be a material that generates a fluorescent or phosphorescent light. The fluorescent material may be, for example, fluorescein, rhodamine, cyanine, a metal porphyrin composite, Cy-5, or Cy-3. Examples of a fluorescein dye may include 6-carboxylfluorescein (6-FAM), 1, 2',4',1,4-tetrachlorofluorescein (TET), 2,2',4',5',7',1,4-hexachlorofluorescein (HEX) 3,2',7'-dimethoxy-4',5'-dichloro-6-carboxyrhodamine (JOE), 4,2'-chloro-5'-fluoro-7',8'-fused phenyl-1,4-dichloro-6-carboxyfluorescein 5, and 2'-chloro-7'-phenyl-1,4-dichloro-6-carboxyfluorescein 6. The enzyme tag may convert a substrate to a chromogenic material. Alternatively, or in addition, the material that specifically binds to PIGR may be immobilized on a substrate (e.g., a bead, column, or plate, or any other solid surface).

The composition may further comprise a second material that specifically binds to at least one breast cancer marker other than PIGR or a fragment thereof. The breast cancer marker may be FasL, CD83, HER2, or any combination thereof.

FasL is also known as a Fas ligand or CD95L, and is a type II transmembrane protein that belongs to the tumor necrosis factor (TNF) family of proteins. The binding of FasL to a receptor thereof may induce apoptosis. FasL is a homotrimer type II transmembrane protein. FasL may transmit a signal through trimerization of a FasL receptor (e.g., FasR) that spans a membrane of a target cell. A soluble FasL may be generated by cleaving the membrane-bound FasL at a conserved cleavage site by an external matrix metalloproteinase MMP-7. FasL may have an amino acid sequence of NP_000630 or NP_001192172. A FasL receptor may be FasR (or CD95), DcR3, or any combination thereof.

CD83 may comprise a protein encoded by a CD83 μlne. CD83 may comprise an amino acid sequence of NP_001035370 or NP_033986.

Human epidermal growth factor receptor 2 (Her2), also known as Neu, ErbB-2, CD340, or p185, may comprise a protein encoded by a ERBB2 μlne in a human body. Her2 is one member of an epidermal growth factor receptor (EGFR/ErbB) family. The ErbB family includes four plasma membrane-bound receptor tyrosine kinases. The four kinases contain an extracellular ligand binding domain, a transmembrane domain, and an intracellular domain that can interacts with many signal transmitting molecules. The members of the family perform ligand-dependent and ligand-independent activities. Her2 may form a heterodimer with any of the other three different receptors and is a preferred dimerization partner of another ErbB receptor. Her2 may have an amino acid sequence of NP_001005862 or NP_001003817.

The composition may be used to contact a sample comprising PIGR or a fragment thereof and FasL or a fragment thereof; PIGR or a fragment thereof, FasL or a fragment thereof, and Her2 or a fragment thereof; PIGR or a fragment thereof and CD83 or a fragment thereof; PIGR or a fragment thereof, CD83 or a fragment thereof, and HER2 or a fragment thereof; or PIGR or a fragment thereof, CD83 or a fragment thereof, and FasL or a fragment thereof, or any combination thereof. The composition may include a combination of the materials specifically binding to one or more breast cancer specific markers. Thus the composition may be used in detection of breast cancer in a sample with specificity and/or sensitivity at a higher degree.

The material that specifically binds to at least one breast cancer marker other than PIGR or a fragment thereof may comprise a detectable tag as previously described herein. Alternatively, or in addition, the material that binds to a breast cancer marker other than PIGR may be immobilized on a substrate. The second material that specifically binds to at least one breast cancer marker other than PIGR or a fragment thereof may be an antibody or an antigen-binding fragment thereof, a ligand, a substrate for an enzyme, an inhibitor, an agonist, an antagonist, a cofactor, or a combination thereof. The antibody may be a monoclonal antibody or a polyclonal antibody. The antigen-binding fragment may include an antigen-binding region which may be, for example, a single-domain antibody, Fab, Fab', or scFv.

The material that specifically binds to PIGR or a fragment thereof and/or the second material that specifically binds to at least one breast cancer marker other than or in addition to PIGR existing or a fragment thereof may be immobilized on a glass or solid support. The solid support may comprise nano or micro particles. The solid support may comprise magnetic or non-magnetic particles. The solid support may be in a form of beads, spheres, polygons, plates, hollow tubes such as a chromatography column, or combinations thereof. The solid support may be an array including the material immobilized on a specific region.

The composition may be in any phase. The composition may comprise a liquid, solid, or any combination thereof.

The subject that is the object of the diagnosis, and from which a sample is obtained, may be a mammal. The mammal may be a human, a mouse, a cow, a pig, a horse, a sheep, a dog, a cat, or a combination thereof.

According to another embodiment, a composition is provided comprising an anti-PIGR antibody or antibody fragment bound to a PIGR or fragment thereof on the surface of a vesicle, wherein the anti-PIGR antibody or antibody fragment is immobilized on a substrate or comprises a detectable label. The composition may comprise a bodily fluid or biological tissue sample.

According to another embodiment, a kit for diagnosing breast cancer is provided, the kit including a material that specifically binds to PIGR or a fragment thereof. The material that specifically binds to a PIGR protein or a fragment thereof, and the PIGR protein itself, is as described above. The kit may additionally comprise a second material that specifically binds to at least one additional cancer marker as described herein.

The kit may comprise instructions (e.g. a protocol) for using a component included in the kit for diagnosing breast cancer. The kit may further include an agent for diagnosing breast cancer in a subject. The agent may include a buffer, an indicator, or any combination thereof.

According to another embodiment of the present invention, provided is a method for diagnosing breast cancer in a subject, the method comprising the steps of: contacting a sample from the subject with a material that specifically binds to PIGR or a fragment thereof present on vesicles in the sample, such that the material binds any vesicles that include PIGR or fragment thereof on their surfaces; measuring the amount of material bound to PIGR or a fragment thereof on the vesicles in the sample, to determine the amount of PIGR or a fragment thereof present in the sample; and comparing the amount of PIGR or fragments thereof in the sample to a control. The contacting step may be performed in a liquid medium. The liquid medium may comprise a liquid sample itself, water, buffer, or any combination thereof. The contacting step may be performed by mixing the sample and the material. The contacting may be performed by stirring the sample and the material in a container. The stirring may be performed at a level that does not destroy a vesicle, such as a microvesicle.

The subject may be a mammal. The mammal may be a primate. The mammal may comprise a human, a human, a mouse, a cow, a pig, a horse, a sheep, a dog, a cat, or a combination thereof.

The sample may comprise a biological material derived from the subject. The biological material may be fresh or preserved solid tissue, such as an organ, a tissue sample, a biopsy sample; blood or components of blood; bodily fluid, such as amniotic fluid, peritoneal fluid, or interstitial fluid; cells; or any combination thereof. The sample may comprise a compound that is not naturally mixed with a biological material, examples of the compound include preservatives, anticoagulants, buffers, fixatives, nutrients, and antibiotics. The sample may comprise, for example, urine, mucus, saliva, tears, blood, plasma, serum, sputum, spinal fluid, pleural fluid, nipple aspirate, lymph fluid, respiratory tract fluid, serous fluid, urogenital fluid, breast milk, lymph secretion, semen, cerebrospinal fluid, body fluid in organs, abdominal fluid, fluid from cystic tumor, amniotic fluid, or any combination thereof.

The method may further include separating a sample from the subject. The subject may be a breast cancer patient. The breast cancer patient may be a patient having a estrogen receptor (ER) positive breast cancer. The estrogen receptor (ER) positive breast cancer may be well differentiated (low grade), moderately differentiated (intermediate grade), or poorly differentiated (high grade). The estrogen receptor (ER) positive breast cancer may be Luminal A, that is ER+ and low grade, or Luminal B, that is, ER+ but often high grade. The receptor status of breast cancers may be identified by immunohistochemistry (IHC), which stains the cells based on the presence of estrogen receptors (ER), progesterone receptors (PR), and HER2. This remains the most common method of testing for receptor status, but DNA multi-gene expression profiles may categorize breast cancers into molecular subtypes that generally correspond to IHC receptor status. Receptor status is a critical assessment for all breast cancers as it determines the suitability of using targeted treatments such as tamoxifen and/or trastuzumab. These treatments are now some of the most effective adjuvant treatments of breast cancer. ER+ cancer cells depend on estrogen for their growth, so they can be treated with drugs to reduce either the effect of estrogen (e.g. tamoxifen) or the actual level of estrogen (e.g. aromatase inhibitors), and generally have a better prognosis.

The grading of a cancer in the breast may depend on the microscopic similarity of breast cancer cells to normal breast tissue, and classify the cancer as well differentiated (low grade), moderately differentiated (intermediate grade), and poorly differentiated (high grade), reflecting progressively less normal appearing cells that have a worsening prognosis. Although grading is fundamentally based on how biopsied, cultured cells behave, in practice the grading of a given cancer is derived by assessing the cellular appearance of the tumor. The closer the appearance of the cancer cells to normal cells, the slower their growth and the better the prognosis. If cells are not well differentiated, they will appear immature, will divide more rapidly, and will tend to spread. Well differentiated is given a grade of 1, moderate is grade 2, while poor or undifferentiated is given a higher grade of 3 or 4 (depending upon the scale used). The Nottingham (also called Elston-Ellis) modification of the Scarff-Bloom-Richardson grading system, may be used, which grades breast carcinomas by adding up scores for tubule formation, nuclear pleomorphism, and mitotic count, each of which is given 1 to 3 points (Elston C W, Ellis I O. Histopathology 1991, 19:403-410). The scores for each of these three criteria may be then added together to give an overall final score and corresponding grade as follows. The grading criteria are as follows:

Tubule formation: This parameter assesses what percent of the tumor forms normal duct structures. In cancer, there is a breakdown of the mechanisms that cells use to attach to each other and communicate with each other, to form tissues such as ducts, so the tissue structures become less orderly. The overall appearance of the tumor may be considered. 1 point: tubular formation in more than 75% of the tumor, 2 points: tubular formation in 10 to 75% of the tumor, and 3 points: tubular formation in less than 10% of the tumor.

Nuclear pleomorphism: This parameter assesses whether the cell nuclei are uniform like those in normal breast duct epithelial cells, or whether they are larger, darker, or irregular (pleomorphic). In cancer, the mechanisms that control genes and chromosomes in the nucleus break down, and irregular nuclei and pleomorphic changes are signs of abnormal cell reproduction. The cancer areas having cells with the greatest cellular abnormalities may be evaluated. 1 point: nuclei with minimal variation in size and shape, 2 points: nuclei with moderate variation in size and shape, 3 points: nuclei with marked variation in size and shape.

Mitotic count: This parameter assesses how many mitotic figures (dividing cells) the pathologist sees in 10× high power microscope field. One of the hallmarks of cancer is that cells divide uncontrollably. The more cells that are dividing, the worse the cancer. Mitotic figures may be counted only at the periphery of the tumor, and counting may begin in the most mitotically active areas. 1 point: 0-9 mitotic counts per 10 fields under X25 objective using the Leitz Ortholux microscope, 0-5 mitotic counts per 10 fields under X40 objective using the Nikon Labophot microscope, or 0-11 mitotic counts per 10 fields under X40 objective using the Leitz Daiplan microscope, 2 points: 10-19 mitotic counts per 10 fields under X25 objective using the Leitz Ortholux microscope, 6-10 mitotic counts per 10 fields under X40 objective using the Nikon Labophot microscope, or 12-22 mitotic counts per 10 fields under X40 objective using the Leitz Daiplan microscope, 3 points: Over 19 mitotic counts per 10 fields under X25 objective using the Leitz Ortholux microscope, over 10 mitotic counts per 10 fields under X40 objective using the Nikon Labophot microscope, or over 22 mitotic counts per 10 fields under X40 objective using the Leitz Daiplan microscope Overall grade: The scores for each of these three criteria are added together to give a final overall score and a corresponding grade as follows: 3-5 Grade 1 tumor (well-differentiated). Best prognosis. 6-7 Grade 2 tumor (moderately-differentiated). Medium prognosis. 8-9 Grade 3 tumor (poorly-differentiated). Worst prognosis. Lower grade tumors, with a more favorable prognosis, may be treated less aggressively, and have a better survival rate. Higher grade tumors may are treated more aggressively, and their intrinsically worse survival rate may warrant the adverse effects of more aggressive medications. The separating may include separating the sample from the site of breast cancer, for example, from the blood vessels or lymph vessel present in the breast tissue. The breast cancer may be ER+ cancer cell, for example, Luminal A or Luminal B. The breast cancer may be stage I or II. The stage may be determined by AJCC (American Joint Committee on Care) cancer staging manual sixth edition.

The material that specifically binds to PIGR or a fragment thereof may comprise a detectable tag.

In methods according to the present invention, the terms "the vesicle", "the material that specifically binds to PIGR or a fragment thereof", and "the detectable tag" used herein are the same as those previously described regarding the composition and the kit.

The measuring step may comprise measuring of presence or an amount of a material specifically binding to PIGR or a fragment thereof while the material is bound to a vesicle, such as a microvesicle. In this case, the material specifically binding to PIGR or a fragment thereof may comprise a detectable tag, and the level of the PIGR or a fragment thereof may be measured determining the presence of a signal from the tag. The measuring step may be performed by measuring presence or amount of the material after separating one or more complexes comprising material specifically bound to microvesicles via PIGR or a fragment thereof as a result of the contacting step.

The measuring step may be performed by directly measuring the amount of the material bound to PIGR or a fragment thereof by separating it from the resultant complexes formed during the contacting step or, alternatively, by indirectly measuring an amount of the material without separating it from the resultant complexes formed during the contacting step. The measuring step may be performed by detecting a signal produced by a detectable tag attached to the material. The separation of the material may be performed by centrifugation, salting-out, dialysis, filtration, chromatography, electrophoresis, or any combination thereof. The chromatography may comprise affinity chromatography, size-exclusion chromatography, ion-exchange chromatography, or a combination thereof. The measuring step may be performed by ELISA, western blotting, electrophoresis, a mass spectrometry, a spectrometer, or a combination thereof.

The method may further include a step of determining whether a subject has breast cancer when amount of the material, and thus the total amount of PIGR or a fragment thereof in the sample, is higher than that of a negative control. The negative control may be provided, for instance, by the PIGR level of a sample from a subject that does not have breast cancer, a subject having a benign tumor, or a subject with no risk of having breast cancer.

The method may comprise comparing an amount of PIGR or a fragment thereof in the vesicles separated from the sample provided by a test subject with the amount of PIGR or a fragment thereof in the vesicles separated from a negative control group sample; and determining the subject has breast cancer or has a risk of developing breast cancer when the amount of PIGR or a fragment thereof is increased compared with the amount of PIGR or a fragment thereof contained in the vesicle separated from the control group sample.

The separation of the vesicle, such as a microvesicle, from the biological sample obtained from the subject may comprise centrifuging the sample obtained from the subject, filtering the biological sample, incubating the vesicle together with a material specifically binding to the vesicle or a material insertable into the lipid bilayer of the vesicle, or any combination thereof. The incubation may be performed in vitro. Additionally, the separating of the vesicle may be performed by, for example, separation using a solid support or a centrifuge force, density gradient centrifugation, ultracentrifugation, filtration, dialysis, immuno-affinity chromatography using an antibody, free-flow electrophoresis, or any combination thereof. The material specifically binding to the vesicle may be a material that may bind to surface protein, lipid, or sugar of a vesicle. The surface protein may comprise CD63, CD83, CD9, integrin-β (ITGB1), EpCAM, caveolin, FasL, HLA-DRA, CD36, CD63, CD81, MUC1, ERBB4, GPER, ERBB2, MLANA, AMHR2, or a combination thereof. The material specifically binding to a vesicle may comprise a material having a binding affinity to proteins, an enzyme-substrate, a coenzyme, a regulatory factor, a material specifically binding to a receptor, lectin, a sugar, a glycoprotein, an antigen, an antibody or an antigen-binding fragment thereof, a hormone, a neurotransmitter, a phospholipid-binding protein, a pleckstrin homology (PH) domain-containing protein, a cholesterol-binding protein, or any combination thereof. The antigen-binding fragment may comprise an antigen-binding region. For example, the antigen-binding fragment may comprise a single-domain antibody, Fab, Fab', or scFv. The material insertable into the lipid bilayer of the vesicle may comprise, for example, a material including a lipophilic moiety, an amphipathic moiety, an amphoteric ion moiety, or a combination thereof. Examples of the lipophilic moiety include fatty acid, sterol, and glyceride. Examples of the amphipathic moiety include phospholipid and sphingolipid. Examples of the amphoteric ion moiety include sulfobetaine, carboxybetaine, and phosphorylcholine.

The material specifically binding to the vesicle or the material insertable into the liquid bilayer of the vesicle may be bound with a solid support. The solid support may the shape of a sphere, a polyhedron, a plate, a bead, or any combination thereof. The solid support may comprise polystyrene, polypropylene, magnetic particle, or any combination thereof.

The method may further include the step of separating the microvesicle and the vesicle from the sample provided by the subject before the contacting step. In this embodiment of the invention, the separating step may not need to involve material that specifically binds to PIGR or a fragment thereof. In this scenario, the amount of vesicles bound with material specifically binding to PIGR or a fragment thereof on the surface of the vesicles in the sample may be compared to the total amount of microvesicles in the sample. The separation of the vesicles in this embodiment may be performed as described above.

The method may further include the steps of washing the vesicles separated from the biological sample, lysing the vesicle separated from the biological sample, or any combination thereof. The lysing of the vesicle may be performed, for example, in the presence of a solvent containing a chaotropic salt, an organic solvent, or a surfactant. The lysing of the vesicle may be performed, for example, by heating, stirring, rotating, vortexing, or any combination thereof.

The method may further include the step of measuring the level of a breast cancer marker other than or in addition to PIGR in the sample. The term "breast cancer marker" as used herein may comprise a compound or a moiety that is specifically found in a breast cancer cell or tissue. The marker may comprise protein or nucleic acid. The nucleic acid marker may comprise miRNA. The marker may be present on a surface of the vesicles, for example, on a surface of microvesicles.

The measuring step may be performed by measuring presence or the amount of the material while the material specifically binds to the breast cancer marker or a fragment thereof, when the breast cancer marker or fragment thereof is bound to a vesicle, such as a microvesicle. In this embodiment of the present invention, the material specifically binding to the marker or a fragment thereof may be comprise a detectable tag, and a level of the marker or a fragment thereof may be estimated by measuring a signal produced by the tag. Additionally, the measuring step may be performed by measuring presence or the amount of the material separated from the complexes of material specifically bound to the marker or a fragment thereof as a result of the contacting step. The term "material specifically binding to a breast cancer marker or a fragment thereof" as used herein is the same as previously described.

The step comprising measuring of the level of the material may be performed by directly measuring an amount of the material by separating it from the resultant product of the contacting step, or indirectly measuring the amount the material without separating it from the resultant products (i.e., material bound to a cancer marker or fragment thereof complexes) of the contacting step. The measuring step may be performed by detecting a signal produced by a detectable tag attached to the material. The separation of the material may be performed by centrifugation, salting-out, dialysis, filtration, chromatography, electrophoresis, or any combination thereof. The chromatography may comprise affinity chromatography, size-exclusion chromatography, ion-exchange chromatography, or a combination thereof. The measuring may be performed by ELISA, western blotting, electrophoresis, a mass spectrometry, a spectrometer, or any combination thereof.

The breast cancer marker may be present on a surface of the vesicle. The breast cancer marker may comprise FasL, CD83, HER2, or any combination thereof.

The method may further include the step of determining the subject has breast cancer when the amount of material specifically binding to PIGR or a fragment thereof (and, thus, the level of vesicle-bound PIGR in the sample) is higher than a negative control, and the breast cancer marker other than PIGR is high compared to those of a negative control. For example, the method may further comprise determining the subject has breast cancer when levels of PIGR or a fragment thereof and FasL or a fragment thereof; PIGR or a fragment thereof, FasL or a fragment thereof, and Her2 or a fragment thereof; PIGR or a fragment thereof and CD83 or a fragment thereof; PIGR or a fragment thereof, CD83 or a fragment thereof, and HER2 or a fragment thereof; or PIGR or a fragment thereof, CD83 or a fragment thereof, and FasL or a fragment thereof are higher in the sample from the subject than in the negative control.

Also provided is a method for obtaining information useful for diagnosing breast cancer of a subject, wherein the method comprises the steps of: contacting a sample from a subject with a material that specifically binds to PIGR or a fragment thereof present on vesicles in the sample; and measuring the amount of the material bound to PIGR or a fragment thereof present on the vesicles in the sample, wherein the amount of material bound to PIGR or a fragment thereof corresponds to the amount of PIGR or a fragment thereof present in the sample.

In the method, the terms "contacting a sample separated from the individual and a material specifically binding to PIGR or a fragment thereof to bind a vesicle in the sample with the material" and "measuring a level of PIGR or a fragment thereof in the vesicle of the sample" are the same with those previously described.

According to another embodiment of the present invention, a composition or a kit for diagnosing breast cancer may be used to efficiently diagnose breast cancer.

According to another embodiment of the present invention, breast cancer in a subject may be efficiently diagnosed by performing a method for diagnosing breast cancer of a subject.

According to another embodiment of the present invention, necessary information for diagnosing breast cancer of a subject may be obtained by performing a method of obtaining information necessary for efficiently diagnosing breast cancer of a subject.

All other aspects of the foregoing methods are as described with respect to the compositions and kits of the invention.

The present invention will be described in further detail with reference to the following examples. These examples are for illustrative purposes only and are not intended to limit the scope of the present invention.

Example 1

Identification of PIGR in Microvesicle as Breast Cancer Marker

Here, a breast cancer marker specifically present in a microvesicle in a blood sample derived from a breast cancer patient was confirmed.

8 ml to 10 ml of a blood sample was taken from each of 20 normal subjects lacking breast cancer and 23 breast cancer patients (stage I or II breast cancer, luminal A or luminal B type) and put into a BD Vacutainer® Plus plastic whole blood tube, and a plasma sample was separated from the sample by performing centrifuge thereon at a temperature of 4° C. and a seed of 1300×g for 10 minutes. The separated plasma sample was preserved at a temperature of −80° C. and was melted, and a supernatant, not precipitate, was used after performing centrifuge thereon at a temperature of 4° C. and a speed of 3000×g for 5 minutes as a sample.

The obtained plasma was pooled and diluted using a PBS buffer having 3 times the volume of the plasma sample. The diluted plasma was sequentially centrifuged at a temperature of 4° C. at a speed of 2,000×g for 30 minutes and at a temperature of 4° C. at a speed of 12,000×g for 30 minutes. Pellets were removed from the centrifuged result, and a supernatant was filtered by using a 0.22 μm filter. The filtered solution was concentrated by using a 300 kDa cut-off membrane column (Vivaproducts) and ultrahigh-speed centrifuged at a temperature of 4° C. and at a speed of 110,000×g for 2 hours to obtain microvesicles as its precipitates.

In order to identify whether an amount of the PIGR in the microvesicles increased or decreased in a breast cancer patient compared to a normal person, an amount of CD63, which is a microvesicle marker, served as an internal control group and was measured to compare with PIGR levels.

The obtained precipitates, i.e., the microvesicles, were suspended in PBS, a lysis buffer, NuPAGE LDS sample buffer (Life Technologies), at pH of 8.4 including lithium dodecyl sulfate was added into the tube, and the microvesicles was subject to a lysis by heat treating the resultant in a heating block at a temperature of 95° C. for 10 minutes. Electrophoresis was performed on the lysate, and western-blotting was performed thereon. The detection from the western-blotting was performed by using a rabbit anti-PIGR antibody (Novus Biologicals) and a rabbit anti-CD63 antibody (Santacruz Biotechnology) as a primary antibody and an HRP-conjugated anti-rabbit antibody as a secondary antibody, and the light-emitting image was analyzed by using Las min 4000 (Fujifilm). A band was detected using a LAS instrument (Fujifilm), and the results are shown in FIG. 1.

As shown in FIG. 1, a band intensity of CD63 was the same in the normal subject group and the breast cancer patient group. However, band intensities of the PIGR significantly increased in the breast cancer patient group, compared to that of the normal subject group. Thus, PIGR in the microvesicle was confirmed to be a breast cancer marker.

Example 2

Identification of PIGR in Surface Protein of Microvesicle as Breast Cancer Marker 8 ml to 10 ml of a blood sample was taken from each of 10 benign tumor (no breast cancer) patients and 10 breast cancer patients (stage II ER+ breast cancer, luminal A or luminal B type) and put into a BD Vacutainer® Plus plastic whole blood tube, and a plasma sample was separated from the sample. The separated plasma sample was preserved at a temperature of −80° C. and was melted, and a supernatant, not precipitate, was used after performing centrifuge thereon at a temperature of 4° C. and a speed of 3000×g for 5 minutes as a sample.

The obtained plasma was pooled, and 300 μl of the pooled sample was mixed with 30 μl of an anti-PIGR antibody-coated bead (0.8 μg of the antibody/1 μl of bead) in a test tube (Axygen). Then, the mixture was incubated by using a Grant Bio rotator at room temperature for 4 hours, and the bead was separated by using a magnetic force. Next, the bead was incubated and washed with 300 μl of PBS at room temperature for 3 hours. The bead was obtained by coating protein G (Sigma) on a Dynabead M-270 Amine (catalog no. 143080, a diameter of 2.8 um, available from Life technologies) bead through a cross-linking reaction by using NHS/EDC, reacting with the anti-PIGR antibody (Novus Biologicals), and coating by using dimethylpimelidate. The obtained bead includes 2×10⁶ beads in 1 µl of PBS.

After removing PBS, 30 µl of a lysis buffer, NuPAGE LDS sample buffer (Life Technologies), at pH of 8.4 including lithium dodecyl sulfate was added into the tube, and the microvesicles was subject to a lysis by heat treating the resultant in a heating block at a temperature of 95° C. for 10 minutes. Electrophoresis was performed on the lysate, and western-blotting was performed thereon. In order to measure an amount of the microvesicles captured by the anti-PIGR antibody, the amounts of integrin-β1 and CD9, which are microvesicle markers, measured by the western blotting using anti-integrin-β1 antibody (Abcam) and anti-CD9 antibody (Novus Biologicals). In particular, the detection was performed by detecting a band using a rabbit anti-integrin-β1 antibody (Abcam) and a rabbit anti-CD9 antibody (Novus Biologicals) as a primary antibody, a HRP-conjugated anti-rabbit antibody as a secondary antibody, and a LAS min 4000 (Fujifilm). The results are shown in FIG. 2 as a graph.

Figure 2:
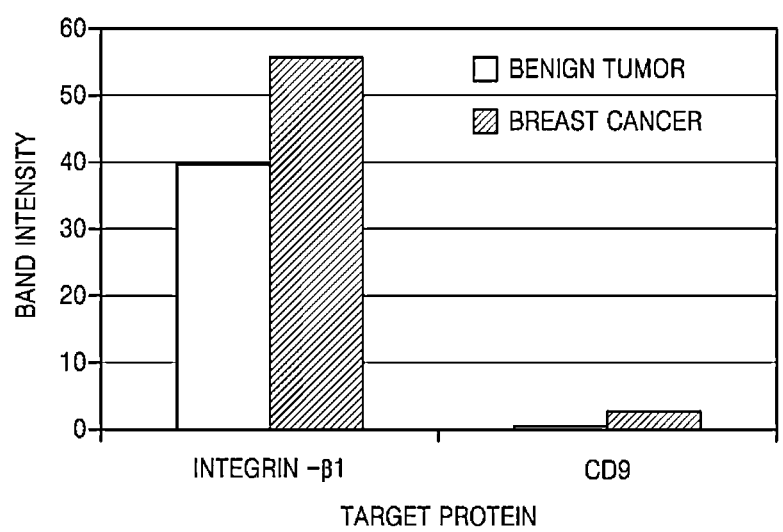
FIG. 2 is a graph displaying the band intensity (Y-axis) of microvesicles that have been separated from samples obtained from benign tumor patients and breast cancer patients through exposure to an anti-PIGR antibody followed by western blotting of the separated microvesicles by an anti-integrin-$\beta1$ antibody and an anti-CD9 antibody.

As shown in FIG. 2, the microvesicles were separated by an anti-PIGR antibody and the amounts of the integrin-β1 and CD9 protein in the separated microvesicles were confirmed by performing western blotting, and thus the amounts of the integrin-β1 and CD9 protein were significantly increased in the breast cancer patient group, compared to the benign tumor patient group. Therefore, a greater amount of the microvesicles in the plasma of the breast cancer patient was captured than that of the benign tumor patient, and it was confirmed that PIGR is more concentrated in the microvesicles related to breast cancer as a surface protein of the microvesicle.

Example 3

Confirmation of Accuracy and Sensitivity of PIGR in Surface Protein of Microvesicle as Breast Cancer Marker 8 ml to 10 ml of a blood sample was taken from each of 19 benign tumor (no breast cancer) patients and 19 breast cancer patients (stage II or III ER+ breast cancer, luminal B type) and put into a BD Vacutainer® Plus plastic whole blood tube, and a plasma sample was separated from the sample by performing centrifuge thereon at a temperature of 4° C. and a speed of 1300×g for 10 minutes, and a plasma sample was separated from the blood sample. The separated plasma sample was preserved at a temperature of −80° C. and was melted, and a supernatant, not precipitate, was used after performing centrifuge thereon at a temperature of 4° C. and a speed of 3000×g for 5 minutes as a sample. The plasma sample was not pooled.

300 µl of the obtained plasma sample was mixed with 30 µl of the anti-PIGR antibody-coated bead. Then, the mixture was incubated at room temperature for 4 hours. 300 µl of the reactant was incubated and washed with PBS at room temperature for 3 hours. The bead was obtained by coating protein G (Sigma) on a Dynabead M-270 Amine (catalog no. 143080, a diameter of 2.8 um, available from Life technologies) bead through a cross-linking reaction by using NHS/EDC, reacting with the anti-PIGR antibody (Novus Biologicals), and coating by using dimethylpimelidate. The obtained bead includes 2×10⁶ beads in 1 µl of PBS.

After removing PBS, 30 µl of a lysis buffer, NuPAGE LDS sample buffer (Life Technologies), at pH of 8.4 including lithium dodecyl sulfate was added into the tube, and the microvesicles was subject to a lysis by heat treating the resultant in a heating block at a temperature of 95° C. for 10 minutes. Electrophoresis was performed on the lysate, and western-blotting was performed thereon. An amount of an integrin-β1, which is a microvesicle marker, was measured by the western blotting in order to confirm an amount of the microvesicles captured by the anti-PIGR antibody. In particular, the detection was performed by detecting a band using a rabbit anti-integrin-β1 antibody (Abcam) as a primary antibody, a HRP-conjugated anti-rabbit antibody as a secondary antibody, and a LAS min 4000 (Fujifilm). A band was detected by using LAS min 4000 (Fujifilm), and band intensities of the integrin-β1 were each quantified by using a program Image J (NCI).

Figure 3A:
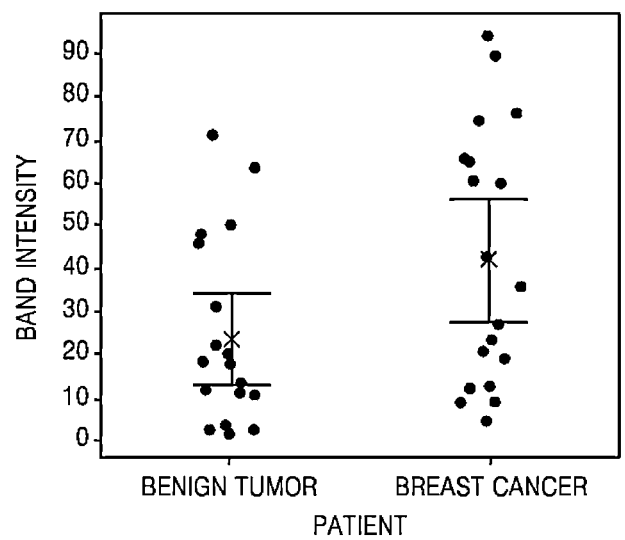
FIGS. 3A and 3B are graphs displaying results of performing band intensity and ROC curve analyses of samples that have had microvesicles separated by an anti-PIGR antibody followed by western blotted by using an anti-integrin-$\beta1$ antibody.

Each of the quantified band intensities of the integrin-β1 for 19 benign tumor patients and 19 breast cancer patients is shown in FIG. 3A as a graph. A value shown in FIG. 3A denotes an average band intensity showing a blot image in the same exposure time, and a p value was 0.034. As shown in FIG. 3A, it was confirmed that an amount of the microvesicle in the plasma captured by the anti-PIGR antibody was significantly increased in the breast cancer patients, which is 42.1032, compared to the benign tumor patients, which is 23.4755.

Figure 3B:
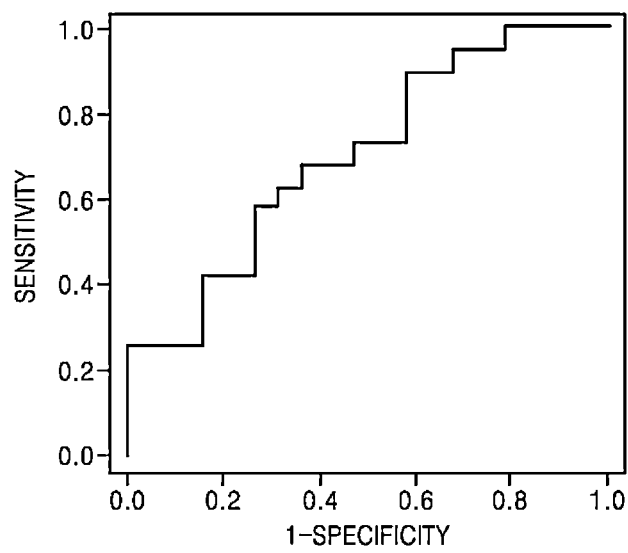

Also, a receiver operating characteristic (ROC) curve analysis was performed using the band intensities of the integrin-β1, and the results are shown in FIG. 3B as a graph. An area under the curve (AUC) of the ROC curve was 0.704.

When sensitivities of a carcinoembryonic antigen (CEA), a cancer antigen (CA) 15-3, and a PIGR obtained from 19 breast cancer patients (stage II or III breast cancer, luminal B type) were examined in the same manner as above, a sensitivity of the CEA was 0.42, a sensitivity of the CA 15-3 was 0, and a sensitivity of the PIGR was 0.68.

Therefore, it was confirmed that PIGR has excellent accuracy and sensitivity as a breast cancer diagnosis marker.

Example 4

Diagnosis of Breast Cancer by Using Breast Cancer Marker Different from PIGR Marker Here, an experiment was performed to determine whether a combination of PIGR in a microvesicle and at least one of FasL, Her2, and CD83 are specifically expressed in the microvesicles of a breast cancer patient.

8 ml to 10 ml of a blood sample was taken from each of 10 benign tumor (no breast cancer) patients and 10 breast cancer patients (stage I or II ER+ breast cancer, luminal B type) and put into an EDTA tube, i.e., a BD Vacutainer® Plus plastic whole blood tube, and a plasma sample was separated from the sample by performing centrifuge thereon at a temperature of 4° C. and a speed of 1300×g for 10 minutes, and a plasma sample removed with blood cells was separated from the blood sample. The separated plasma sample was preserved in a super low temperature refrigerator at a temperature of −80° C. and was melted, and a supernatant, not precipitate (lipid and cell debris), was used after performing centrifuge thereon at a temperature of 4° C. and a speed of 3000×g for 5 minutes as a sample. Before performing the experiment, the plasma sample obtained from each of 10 benign tumor (no breast cancer) patients, 10 breast cancer patients of stage I breast cancer, and 10 breast cancer patients of stage II breast cancer was pooled to obtain 3 groups of plasmas, and the experiment was performed on each of the groups.

300 μl of the obtained plasma sample was mixed with 30 μl of a magnetic bead coated with a predetermined antibody. Then, the mixture was incubated at room temperature for 4 hours to perform immunoprecipitation. 300 μl of the reactant was incubated and washed with PBS at room temperature for 3 hours. The bead was obtained by coating protein G (Sigma) on a Dynabead M-270 Amine (catalog no. 143080, a diameter of 2.8 um, available from Life technologies) bead through a cross-linking reaction by using NHS/EDC. Then, 30 μl of the protein G-coated bead was reacted with 80 ug of the antibody the anti-PIGR antibody (Novus Biologicals), and coated by using dimethylpimelidate. The antibody used in the coating may be an anti-PIGR (Novus biological) antibody, an anti-CD83 antibody, an anti-FasL antibody (BD Pharmingen), an anti-HER2 antibody (R&D Systems), or a combination thereof. When the combination is used, each of the antibody was used at the same amount so as the total weight to be 80 ug. The obtained bead includes $2 \times 10^6$ beads in 1 μl of PBS.

After removing PBS, 30 μl of a lysis buffer, NuPAGE LDS sample buffer (Life Technologies), at pH of 8.4 including lithium dodecyl sulfate was added into the tube, and the microvesicles was subject to a lysis by heat treating the resultant in a heating block at a temperature of 95° C. for 10 minutes. Electrophoresis was performed on the lysate, and western-blotting was performed thereon. An amount of an integrin-β1, which is a microvesicle marker, was measured by the western blotting in order to confirm an amount of the microvesicles captured by the anti-PIGR antibody. In particular, the detection was performed by detecting a band using a rabbit anti-integrin-β1 antibody (Abcam) as a primary antibody, a HRP-conjugated anti-rabbit antibody as a secondary antibody, and a LAS min 4000 (Fujifilm). A band was detected by using LAS min 4000 (Fujifilm), and band intensities of the integrin-β1 were each quantified by using a program Image J (NCI).

Figure 4:
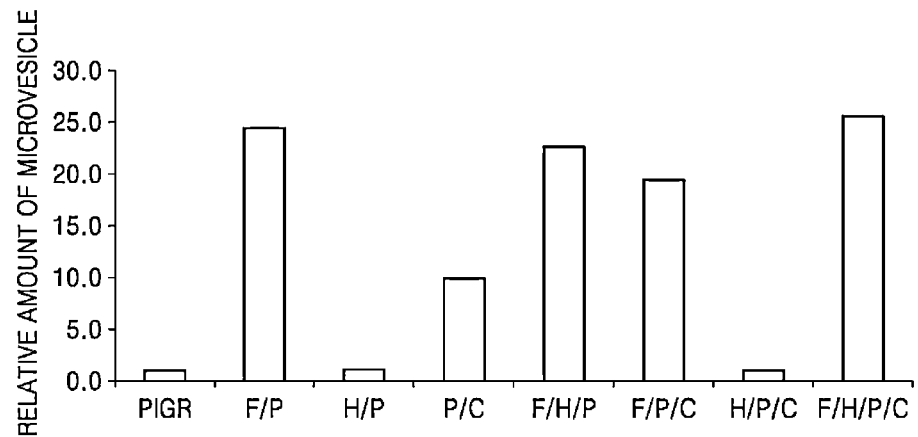
FIG. 4 is a diagram illustrating the relative amounts of microvesicles separated (Y-axis) by magnetic beads coated with various antibodies that were exposed to a plasma equivalent mixed from the plasma separated from 10 breast cancer stage II patients.

FIG. 4 is a diagram illustrating a relative amount of a microvesicles separated by using magnetic beads coated with indicated antibodies from a plasma pool obtained by mixing each equivalent volume of the plasma separated from 10 breast cancer patients having stage II ER+ breast cancer, luminal B type. In FIG. 4, values of the Y-axis are relative values with respect to values obtained from experiments using an anti-PIGR antibody. F/P, H/P, P/C, F/H/P, F/P/C, H/P/C, and F/H/P/C of the X-axis each respectively show cases of using an anti-FasL (F) antibody and an anti-PIGR antibody (P); an anti-Her2 antibody (H) and an anti-PIGR antibody (P); an anti-PIGR antibody (P) and an anti-CD83 antibody (C); an anti-FasL antibody (F), an anti-Her2 antibody (H), and an anti-PIGR antibody (P); an anti-FasL antibody (F), an anti-PIGR antibody (P), and an anti-CD83 antibody (C); and an anti-FasL antibody (F), an anti-Her2 antibody (H), an anti-PIGR antibody (P), and an anti-CD83 antibody (C). As shown in FIG. 4, when an anti-breast cancer marker antibody other than an anti-PIGR antibody is used in a combination with an anti-PIGR antibody, an amount of the immune-precipitated microvesicle is increased to 25.6 times as greater as the case when the anti-PIGR antibody is used alone. That is, when the antibodies are used in a combination, a separation efficiency of the breast cancer microvesicle is increased to 25.6 times as greater as the case when the anti-PIGR antibody is used alone.

Table 1 shows the relative amount of microvesicle compared with that of PIGR marker as shown in FIG. 4.

TABLE 1

| | Marker or marker combination | | | | | | | |
|---|---|---|---|---|---|---|---|---|
| | PIGR | F/P | H/P | P/C | F/H/P | F/P/C | H/P/C | F/H/P/C |
| the relative amount of microvesicle | 1.0 | 24.4 | 1.1 | 9.9 | 22.6 | 19.5 | 1.0 | 25.6 |

Figure 5:
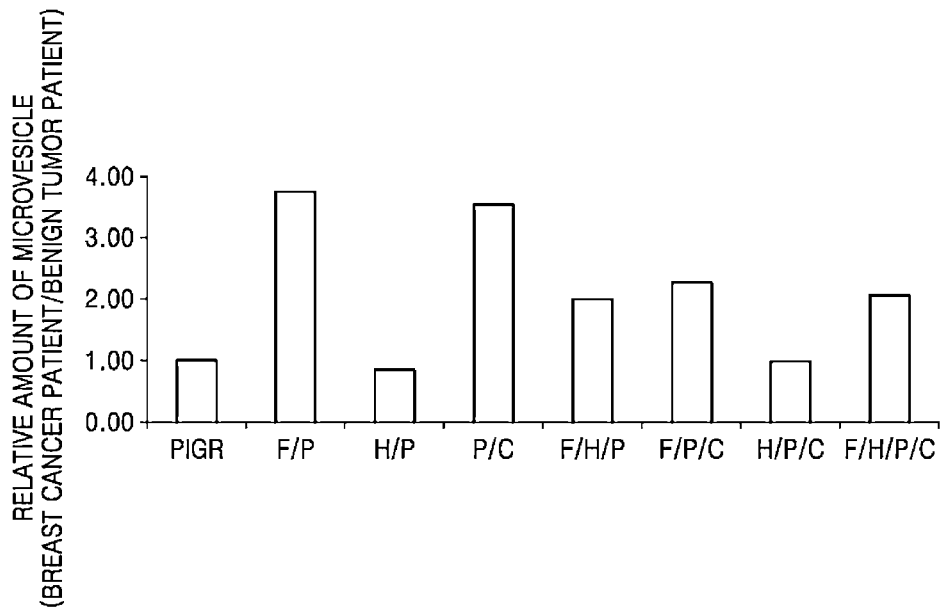
FIG. 5 is a diagram illustrating the relative amounts of microvesicles separated (Y-axis) by magnetic beads coated with various antibodies that were exposed to a plasma equivalent mixed from the plasma separated from 10 breast cancer stage II patients and 10 benign tumor patients.

FIG. 5 is a diagram illustrating a relative amount of microvesicles separated by magnetic beads coated with indicated antibodies from a plasma pool obtained by mixing an equivalent volume of the plasma separated from 10 breast cancer patients having stage II ER+ breast cancer, luminal B type, compared to the amount of microvesicles separated by magnetic beads coated with indicated antibodies from a plasma pool obtained by mixing an equivalent volume of the plasma separated from 10 benign tumor patients. In FIG. 5, values of the Y-axis indicates the relative amount of microvesicles separated by magnetic beads coated with indicated antibodies from a plasma pool obtained by mixing an equivalent volume of the plasma separated from 10 breast cancer patients having stage II ER+ breast cancer, luminal B type in comparison to those of 10 benign tumor patients, and then normalized against the relative amount obtained by using magnetic beads coated with anti-PIGR antibody. F/P, H/P, P/C, F/H/P, F/P/C, H/P/C, and F/H/P/C of the X-axis each respectively show cases of using an anti-FasL antibody and an anti-PIGR antibody; an anti-Her2 antibody and an anti-PIGR antibody; an anti-PIGR antibody and an anti-CD83 antibody; an anti-FasL antibody, an anti-Her2 antibody, and an anti-PIGR antibody; an anti-FasL antibody, an anti-PIGR antibody, and an anti-CD83 antibody; and an anti-FasL antibody, an anti-Her2 antibody, an anti-PIGR antibody, and an anti-CD83 antibody. As shown in FIG. 5, when an anti-breast cancer antibody other than an anti-PIGR antibody are used in a combination, an identifying ability of breast cancer increased to 3.74 times as greater as the case when the anti-PIGR antibody is used alone. Table 2 shows the relative amount of microvesicles as shown in FIG. 5.

TABLE 2

| | Marker or marker combination | | | | | | | |
|---|---|---|---|---|---|---|---|---|
| | PIGR | F/P | H/P | P/C | F/H/P | F/P/C | H/P/C | F/H/P/C |
| the relative amount of microvesicle | 1.0 | 3.74 | 0.85 | 3.54 | 1.99 | 2.27 | 0.99 | 2.06 |

Figure 6:
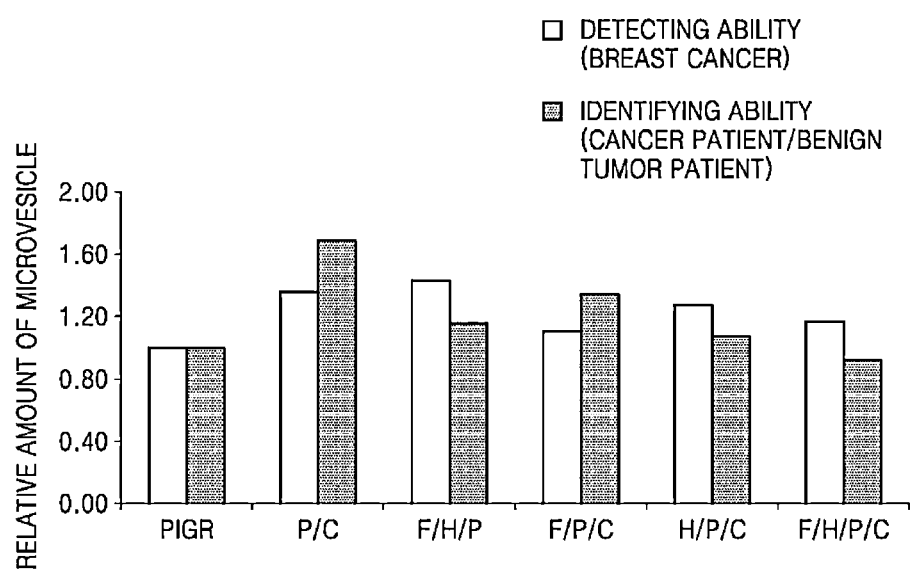
FIG. 6 is a diagram illustrating a relative amounts of a microvesicles separated (Y-axis) by magnetic bead coated with various antibodies that were exposed to a plasma equivalent mixed from the plasma separated from 10 breast cancer stage I patients and 10 benign tumor patients.

FIG. 6 is a diagram illustrating the relative amount of a microvesicles separated by magnetic beads coated with indicated antibodies from a plasma pool obtained by mixing an equivalent volume of the plasma separated from 10 breast cancer patients having stage I ER+ breast cancer, luminal B type cell (left white bar) and the relative amount of a microvesicles separated by magnetic beads coated with indicated antibodies from a plasma pool obtained by mixing an equivalent volume of the plasma separated from 10 breast cancer patients having stage I ER+ breast cancer cell, luminal B type compared to those of 10 benign tumor patients (right black bar). In FIG. 6, values of the Y-axis indicate a relative amount of a microvesicles separated by magnetic beads coated with indicated antibodies from a plasma pool obtained by mixing an equivalent volume of the plasma separated from 10 breast cancer patients having stage I ER+ breast cancer cell compared to an amount of a microvesicles separated by magnetic beads coated with anti-PIGR antibodies (left white bar) and a relative amount of microvesicles separated by magnetic beads coated with indicated antibodies from a plasma pool obtained by mixing an equivalent volume of the plasma separated from 10 breast cancer patients having stage I ER+ breast cancer compared to those of 10 benign tumor patients, and then normalized with the relative amount obtained by using magnetic beads coated with anti-PIGR antibody. F/P, H/P, P/C, F/H/P, F/P/C, H/P/C, and F/H/P/C of the X-axis each respectively show cases of using an anti-PIGR antibody and an anti-CD83 antibody; an anti-FasL antibody, an anti-Her2 antibody, and an anti-PIGR antibody; an anti-FasL antibody, an anti-PIGR antibody, and an anti-CD83 antibody; and an anti-FasL antibody, an anti-Her2 antibody, an anti-PIGR antibody, and an anti-CD83 antibody. As shown in FIG. 6, when an anti-breast cancer antibody other than an anti-PIGR antibody are used in a combination, a detecting ability of a breast cancer specific microvesicle is increased to 1.43 times, and an identification ability to 1.69 times as greater as the case when the anti-PIGR antibody is used alone.

Table 3 shows the relative amount of microvesicles as shown in FIG. 6.

TABLE 3

| | Marker or marker combination | | | | | |
| --- | --- | --- | --- | --- | --- | --- |
| | PIGR | P/C | F/H/P | F/P/C | H/P/C | F/H/P/C |
| Detecting ability | 1.00 | 1.36 | 1.43 | 1.10 | 1.27 | 1.17 |
| Identifying ability | 1.00 | 1.69 | 1.16 | 1.34 | 1.08 | 0.92 |

As described above, according to one or more embodiments of the present invention, a composition and a kit for breast cancer diagnosis including a material that specifically binds to a PIGR protein or a fragment thereof, and methods for diagnosing breast cancer or acquiring information for breast cancer diagnosis by using said compositions or kits may allow for the early diagnosis of breast cancer in a less invasive manner, and thus may be more convenient for patients.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for detecting breast cancer in a subject, the method comprising the steps of:
   contacting a sample from blood, nipple aspirate or ductal lavage comprising vesicles from a subject with an anti-PIGR antibody or antibody fragment, wherein the anti-PIGR antibody or fragment thereof binds to vesicles that comprise PIGR to form a complex of the anti-PIGR antibody or fragment thereof, PIGR or fragment thereof, and vesicle;
   measuring the amount of the complex formed to determine the amount of PIGR or a fragment thereof present in the sample; and
   comparing the amount of PIGR or fragment thereof in the sample to a control, wherein breast cancer is indicated when the amount of PIGR or a fragment thereof in the sample is higher than that of a negative control, wherein the negative control is the PIGR level of a cancer-free subject measured under the same conditions as used to measure the PIGR level of the sample from the subject;
   wherein the method further comprises separating the vesicles from the sample before or after contacting the sample with the anti-PIGR antibody or a fragment thereof and before the step of measuring the amount of the complex formed.

2. The method of claim 1, wherein the separating step is performed by removing complexes of the anti-PIGR antibody of fragment therof, PIGR, and vesicle from the sample.

3. The method of claim 1, wherein the anti-PIGR antibody or antibody fragment comprises a detectable tag.

4. The method of claim 1, further comprising measuring the amount of a breast cancer marker other than PIGR in the sample.

5. The method of claim 4, wherein the method further comprises measuring the level of one or more breast cancer markers selected from the group consisting of FasL, CD83, HER2, or any combination thereof.

6. The method of claim 4, wherein breast cancer is indicated when the PIGR level and the level of the breast cancer marker other than PIGR is higher than that of a negative control.

7. A method of determining PIGR levels in a subject, the method comprising
    contacting a sample from blood, nipple aspirate or ductal lavage comprising vesicles from a subject with an anti-PIGR or fragment thereof wherein the anti-PIGR antibody or fragment thereof binds to vesicles that comprise PIGR to form a complex of the anti-PIGR antibody or fragment thereof, PIGR or fragment thereof, and vesicle; and measuring the amount of the complex formed to determine the amount of PIGR or a fragment thereof present in the sample;
    wherein the amount of PIGR or a fragment thereof present in the sample is indicative of PIGR level in the subject
    and wherein the method further comprises separating the vesicles from the sample before or after contacting the sample with the anti-PIGR antibody or a fragment thereof and before the step of measuring the amount of the complex formed.

8. The method of claim 7, wherein the anti-PIGR antibody or fragment thereof comprises a detectable tag.

9. The method of claim 1, wherein the anti-PIGR antibody or a fragment thereof is immobilized on a substrate.

10. The method of claim 7, wherein the anti-PIGR antibody or a fragment thereof is immobilized on a substrate.

\* \* \* \* \*